(12) United States Patent
Pratt

(10) Patent No.: US 10,206,729 B2
(45) Date of Patent: Feb. 19, 2019

(54) SELF-LOCKING CABLE GRIPPER

(71) Applicant: KINAMED, INC., Camarillo, CA (US)

(72) Inventor: Clyde R. Pratt, Somis, CA (US)

(73) Assignee: KINAMED, INC., Camarillo, CA (US)

( * ) Notice: Subject to any disclaimer, the term of this patent is extended or adjusted under 35 U.S.C. 154(b) by 619 days.

(21) Appl. No.: 14/586,435

(22) Filed: Dec. 30, 2014

(65) Prior Publication Data

US 2016/0183991 A1    Jun. 30, 2016

(51) Int. Cl.
   A61B 17/82    (2006.01)
   A61B 17/88    (2006.01)
   F16G 11/10    (2006.01)
   A61B 17/04    (2006.01)

(52) U.S. Cl.
   CPC .......... *A61B 17/82* (2013.01); *A61B 17/8869* (2013.01); *F16G 11/105* (2013.01); *A61B 2017/0451* (2013.01)

(58) Field of Classification Search
   CPC ..... A61B 17/82–17/826; A61B 17/842; A61B 17/8675; E04C 5/122
   See application file for complete search history.

(56) References Cited

U.S. PATENT DOCUMENTS

| | | | |
|---|---|---|---|
| 3,952,377 A * | 4/1976 | Morell | E04C 5/122 24/136 R |
| 3,975,799 A * | 8/1976 | Kerr | E04C 5/122 24/115 M |
| 5,908,421 A | 6/1999 | Beger | |
| 6,589,246 B1 | 7/2003 | Hack et al. | |
| 7,043,801 B2 * | 5/2006 | Toimil | F16G 11/106 24/136 R |
| 7,207,090 B2 | 4/2007 | Mattchen | |
| RE43,194 E | 2/2012 | Toimil | |
| 8,469,967 B2 | 6/2013 | Pratt et al. | |

(Continued)

FOREIGN PATENT DOCUMENTS

| | | |
|---|---|---|
| DE | 9108810 U1 | 10/1991 |
| FR | 1403335 A | 6/1965 |
| WO | WO2005035407 A2 | 4/2005 |

OTHER PUBLICATIONS

Office Action for Swedish Patent Application No. 1750969-6, dated Apr. 13, 2018.

(Continued)

*Primary Examiner* — Olivia C Chang
(74) *Attorney, Agent, or Firm* — M. J. Ram and Associates

(57) ABSTRACT

A self-locking cable gripper includes a housing having a void which tapers between openings at the housing's top and bottom. A collapsible member having a central passage is adjacent the bottom opening. A pair of half jaws are between the collapsible member and the top opening, sized such that they move towards each other as the jaws are moved toward the bottom opening due to the taper of the void. The top and bottom openings, central passage, and inner surfaces of the jaws define a channel capable of receiving a cable passed through the housing from its bottom to its top opening. When the cable is pulled in the direction opposite that with which it was installed, the half jaws are drawn toward the housing's bottom opening such that their inner surfaces are urged towards each other, thereby locking the cable in place while it is under tension.

36 Claims, 3 Drawing Sheets

(56) References Cited

U.S. PATENT DOCUMENTS

| | | |
|---|---|---|
| 9,107,720 B2 | 8/2015 | Pratt et al. |
| 9,481,972 B1* | 11/2016 | Mullins .................. E02D 5/526 |
| 2002/0129570 A1* | 9/2002 | Sorkin ..................... E04C 5/12 |
| | | 52/223.13 |
| 2007/0074378 A1 | 4/2007 | Tamm et al. |
| 2010/0305571 A1* | 12/2010 | Pratt .................. A61B 17/8869 |
| | | 606/74 |
| 2011/0084180 A1 | 4/2011 | Toimil et al. |

OTHER PUBLICATIONS

Swedish Search Report for Patent Application No. 1750969-6, dated Apr. 13, 2018.

* cited by examiner

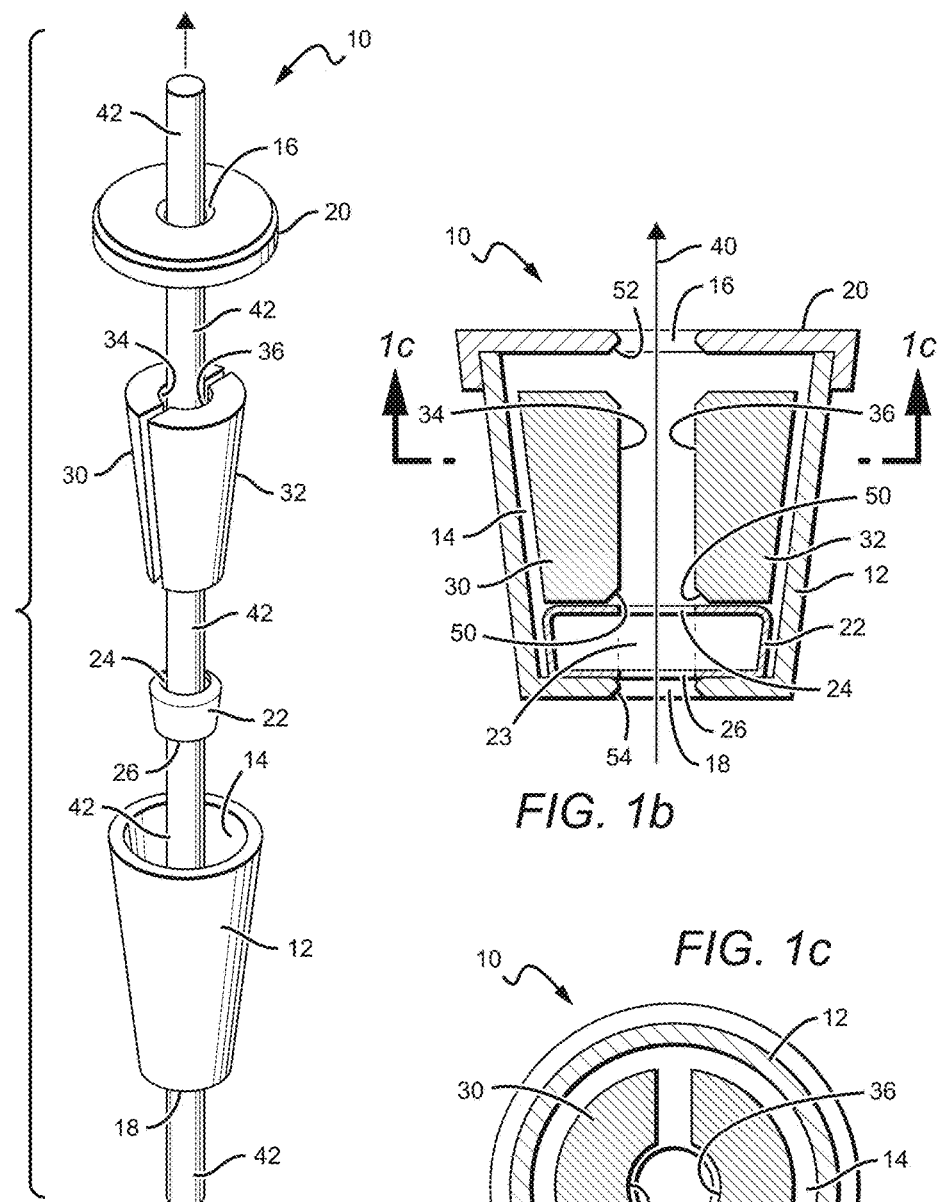

SELF-LOCKING CABLE GRIPPER

BACKGROUND OF THE INVENTION

Field of the Invention

This invention relates to devices for locking cables against longitudinal movement generally, and more specifically to devices for retaining surgical cables under high tension, suitable for surgical implantation in a human body.

Description of the Related Art

Many products are known which serve to hold human body tissues and bones in a desired relationship or position, to aid in their healing when injured or diseased. One such product is the surgical cable, which is wrapped around one or more tissues and/or bones as needed. For example, a surgical cable can be wrapped around the fragments of a fractured bone, such that a compressive force is applied which aids in the healing of the bone. Such a cable is described, for example, in U.S. Pat. No. 6,589,246 to Hack et al.

Once a surgical cable has been wrapped around the tissues to be compressed, a means of holding and locking the cable in place must be employed. Cable locks based on the principle of the wedge are known. Consider, for example, the lock described in U.S. Pat. No. 7,207,090 to Mattchen. Such cable locks employ a wedge as a simple machine for securing cordage.

Another cable locking device is disclosed in US RE43,194 to Toimil. Here, a pair of serrated half jaws, a spacer and a spring are arranged in a housing with a conical-shaped passageway, through which a cable to be secured is threaded. The jaws and spring operate to secure and lock the cable in place such that movement is only allowed in one direction.

SUMMARY OF THE INVENTION

A self-locking cable gripper is presented, which is suitable for retaining flexible cables such as surgical cables at high load tensions.

The present cable gripper includes a housing having a void which runs between openings at the housing's top and bottom, which tapers from a wider portion adjacent the top opening to a narrower portion adjacent the bottom opening. A collapsible member is positioned within the housing, adjacent to the housing's bottom opening. The collapsible member has a central passage which runs between a top and bottom opening, with the housing's bottom opening sized to retain the collapsible member within the housing.

A pair of half jaws are positioned within the housing between the collapsible member and the housing's top opening. The half jaws are sized such that their inner surfaces are urged towards each other when the jaws are moved toward the housing's bottom opening, due to the taper of the void. The housing's top opening is sized to retain the half jaws within the housing. The housing's top and bottom openings, the collapsible member's top and bottom openings, the central passage, and the inner surfaces of the jaws define a channel capable of receiving a cable passed through the housing from its bottom opening to its top opening.

A cable gripper as described herein is installed on a cable by inserting the cable into the housing's bottom opening and pulling it through the housing's top opening. The gripper is arranged such that when the cable is pulled in the direction opposite that with which it was installed, the half jaws are drawn toward the housing's bottom opening such that their inner surfaces are urged towards each other, thereby locking the cable in place while it is under tension.

The collapsible member is preferably arranged to maintain the half jaws in the wider portion of the void in an 'open' position while a cable is being passed through the housing from its bottom opening to its top opening, and to collapse and thereby allow the half jaws to move toward the housing's bottom opening and press together into a 'closed' position when the cable is pulled in the opposite direction.

These and other features, aspects, and advantages of the present invention will become better understood with reference to the following description and claims.

BRIEF DESCRIPTION OF THE DRAWINGS

FIG. 1a is an exploded perspective view of a self-locking cable gripper in accordance with the present invention.

FIGS. 1b and 1c are cutaway and sectional views, respectively, of a self-locking cable gripper in accordance with the present invention, shown in its 'open' position.

DETAILED DESCRIPTION OF THE INVENTION

Figure 1D:
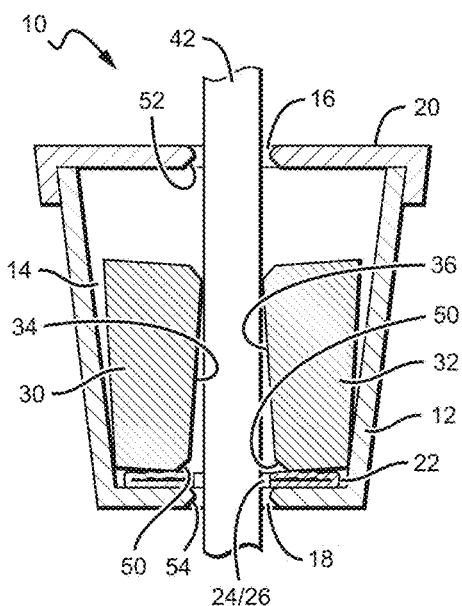
FIG. 1d is a cutaway view of a self-locking cable gripper in accordance with the present invention, shown in its 'closed' position.

The present self-locking cable gripper is suitable for use retaining flexible cables, such as surgical cables, under a tension load. The cable gripper permits passage of the cable through the device in a first direction, but acts to lock the cable and prevent it from moving when pulled in the opposite direction.

An exploded perspective view of one possible embodiment of the present self-locking cable gripper 10 is shown in FIG. 1a, with corresponding cutaway and sectional views shown in FIGS. 1b and 1c. The gripper is contained with a housing 12, which includes a void 14 that runs between a top opening 16 and a bottom opening 18. The void 14 tapers from a wider portion adjacent top opening 16 to a narrower portion adjacent bottom opening 18. Top opening 16 is preferably provided as a hole through a top cap 20, which can be permanently attached to housing 12 but which is preferably removable, which is installed over the top of housing 12 when the gripper is assembled.

A collapsible member 22 is positioned within housing 12, adjacent to the housing's bottom opening 18. The collapsible member has a central passage 23 which runs between a top opening 24 and a bottom opening 26. The housing's bottom opening 18 is sized to retain collapsible member 22 within the housing. When the gripper is fully assembled, the collapsible member nestles within the narrow portion of void 14 at the bottom of housing 12, with its central passage aligned with the housing's bottom opening 18.

A pair of half jaws 30, 32 are positioned within housing 12 between the top of collapsible member 22 and the housing's top opening 16. The half jaws are sized such that, when moved toward the housing's bottom opening 18, the inner surfaces 34, 36 of the jaws are urged towards each other due to the taper of the void 14. The housing's top opening 16 is sized to retain the half jaws within housing 12 when the cable gripper is fully assembled.

The housing's top and bottom openings 16, 18, the collapsible member's top and bottom openings 24, 26, the central passage 23, and the inner surfaces 34, 36 of the half jaws define a channel 40 capable of receiving a cable 42 (shown in FIG. 1*a*) passed through housing 12, when the cable is inserted via the housing's bottom opening 18 and threaded through the gripper and out the top opening 16.

Collapsible member 22 is arranged to maintain half jaws 30, 32 in the wider portion of the tapered void 14 and in an 'open' position—i.e., with the inner jaw surfaces 34, 36 spaced apart such that a cable can be easily threaded between them—while a cable is being passed through housing 12 from its bottom opening 18 to its top opening 16. The half jaws are preferably arranged such that their inner jaw surfaces barely contact a cable being threaded through the gripper. Collapsible member 22 is further arranged to collapse and thereby allow half jaws 30, 32 to move toward the housing's bottom opening 18 and press together into a 'closed' position—i.e., with the cable pinched and therefore locked between the inner jaw surfaces—when the cable is pulled in the opposite direction. Collapsible member 22 collapses over and into bottom opening 18, and thus serves to 'seal' the cable gripper. FIG. 1*d* illustrates half jaws 30, 32 in the 'closed' position.

Collapsible member 22 can have any shape, as long as it serves the functions noted above. One suitable shape for collapsible member 22 is a dome, with the rounded dome portion in contact with and supporting half jaws 30, 32 when in their 'open' position, and collapsing as the half jaws move downward when a cable is pulled in the opposite direction such that the half jaws are allowed to move into their 'closed' position. Collapsible member 22 preferably comprises polyethylene, such as HDP or UHMWP/E.

The inner surfaces 34, 36 of half jaws 30, 32 (i.e., the portions of the half jaws which define channel 40) are preferably textured to provide a friction surface, so as to improve the security with which a cable is locked when the jaws are 'closed'. An aggressive blast surface may provide sufficient friction, though other macro features such as stepped wedges might also be used. For example, inner surfaces 34, 36 could be serrated, with the teeth angled so as to not impede a cable 42 being passed through housing 12 from bottom opening 18 to top opening 16, and to catch on the cable as half jaws 30, 32 move toward the housing's bottom opening when the cable is pulled in the opposite direction. The friction surface helps to draw the half jaws down into the bottom of the housing and thereby lock the cable when it is under tension.

As shown in FIG. 1*b*, the inner surfaces 34,36 of the half jaws immediately adjacent to collapsible member 22 may be beveled 50, to ease the passage of a cable through housing 12 from bottom opening 18 to top opening 16. For the same reason, the bottom surface 52 of the housing's top opening 16, and the bottom surface 54 of bottom opening 18, may also be beveled. The top surface of the housing's top opening 16 may also be beveled, so that undue stresses are not created in the cable when under tension and exiting the housing at an angle.

The outer surfaces of the half jaws 30,32 are preferably polished such that they slide easily within housing 12, so as to minimize the creation of wear debris and corrosion products. Similarly, the inner surface of housing 12 is preferably polished such that the half jaws slide easily within the housing so as to minimize the creation of wear debris and corrosion products.

Housing 12, cap 20 and half jaws 30, 32 can be made from, for example, metal or metallic alloys such as titanium or a titanium alloy, and/or an engineered high strength polymer such as PEEK. These components can be made from a polymer, both can be metal-based, or the housing/cap can be a metal such as titanium and the half jaws from a polymer such as PEEK.

If both the housing and half jaws are made from metallic alloys, the housing and half jaws are preferably manufactured from the same metallic alloy, so as to minimize galvanic corrosion. Polishing the metal/metal interface surfaces as mentioned above helps to reduce fretting corrosion, which is exacerbated if there is a metallic couple of different potential.

A cable gripper with a metal housing/cap and polymer jaws would not generate metallic debris, as the sliding components would be plastic.

Figure 2:
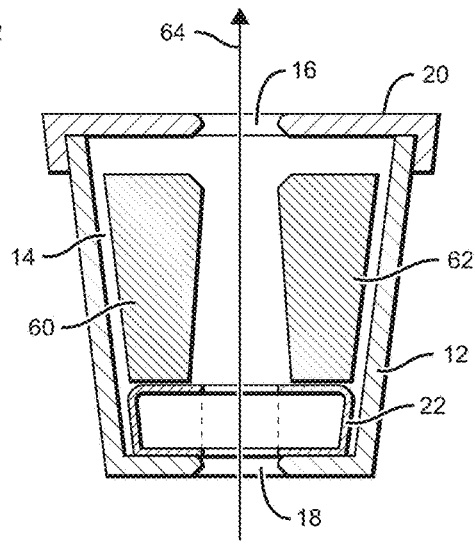
FIG. 2 is a sectional view of another possible embodiment of the present cable gripper.

Another way to ease the passage of a cable through housing 12 is shown in FIG. 2. Whereas channel 40 in FIGS. 1*a*-1*c* is essentially cylindrical, here half jaws 60, 62 are arranged such that when 'open', the channel 64 through them is slightly tapered—with the channel being wider at the bottom than at the top. The degree of taper when the half jaws are in the 'open' position is preferably 3° or less.

Housing 12 is preferably conical, with its top opening 16 and bottom opening 18 being circular and the central passage through collapsible member 22 being cylindrical. However, other housing shapes might also be used as long the inner walls of the housing taper, such that the inner surfaces of the half jaws are urged towards each other as the jaws are moved toward the narrower end of the housing. For example, housing 12 might have a square cross-section, as long at least two opposing walls of the housing are tapered as described above.

Figure 3:
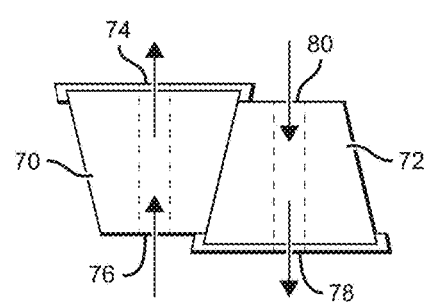
FIG. 3 is a plan view of a clasp assembly which employs two self-locking cable grippers in accordance with the present invention, with the grippers oriented in opposite directions.

Two or more self-locking cable grippers as described above may be assembled into a clasp assembly, with the individual grippers arranged adjacent to each other and oriented such that their respective channels are parallel to each other. As illustrated in FIG. 3, a clasp assembly could be arranged with first and second grippers 70, 72, with the orientation of the top and bottom openings (74, 76) of the first gripper being opposite the orientation of the top and bottom openings (78, 80) of the second gripper. This arrangement is useful for securing a single circular cable; for example, one end of a cable might be threaded through gripper 70, with the cable's other end then wrapped around anatomical structures to be held together and threaded through gripper 72. The cable is tightened and locked by pulling on one or both of its ends, as the grippers 70, 72 will prevent the cable from moving in the opposite direction.

Figure 4:
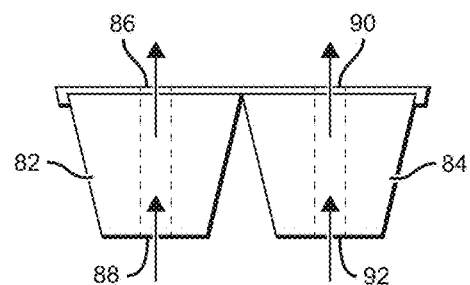
FIG. 4 is a plan view of a clasp assembly which employs two self-locking cable grippers in accordance with the present invention, with the grippers oriented in the same direction.

Alternatively, as illustrated in FIG. 4, a clasp assembly could be arranged with first and second grippers 82, 84, with the orientation of the top and bottom openings (86, 88) of the first gripper being the same as the orientation of the top and bottom openings (90, 92) of the second gripper. This arrangement is useful for allowing movement in only one direction for two single cables.

Figure 5:
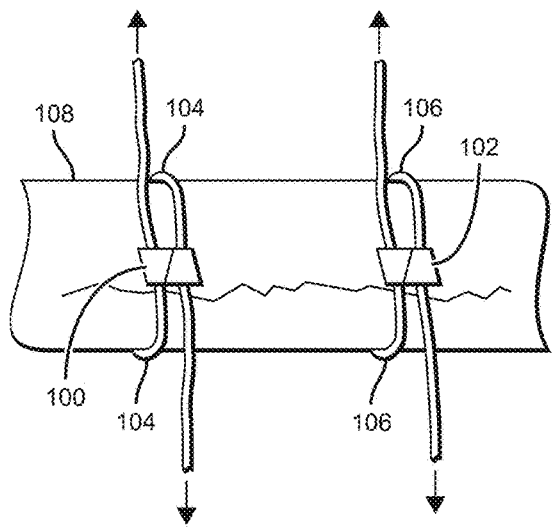
FIG. 5 is perspective view illustrating the use of multiple clasp assemblies to apply tension to an anatomical structure.

As noted above, a cable is inserted into and through a gripper in a first direction, and can be locked into position by simply pulling on the cable in the opposite direction. No additional tensioning device or hardware is necessary. One advantage of this locking mechanism is illustrated in FIG. 5. Here, two clasps 100, 102 are employed, each with a pair of oppositely-oriented grippers (as per FIG. 3). Two cables 104, 106 are wrapped around an anatomical structure such as a fractured bone 108, with the opposing ends of cable 104 routed through the grippers of clasp 100, and the ends of cable 106 routed through the grippers of clasp 102. When so arranged, each cable may be tightened around the bone by pulling on its free ends in the direction indicated, preferably simultaneously. In practice, many such cable/clasp combinations may be employed on a particular structure; a surgeon or other designated person may perform an initial tensioning by pulling on the opposing ends of each cable that has been installed, and then go back and selectively increase the tension on one or more of the installed cables by again pulling on the opposing ends. This could be repeated as many times as needed.

The present self-locking cable gripper could also be employed in the manner of a cartridge which can be placed on or within a component to enable a surgical cable to be secured to the component. For example, a gripper in cartridge form could be affixed to a bone plate, a prosthesis or a surgical anchor, thereby enabling one or more cables to be secured to the component.

Figure 6:
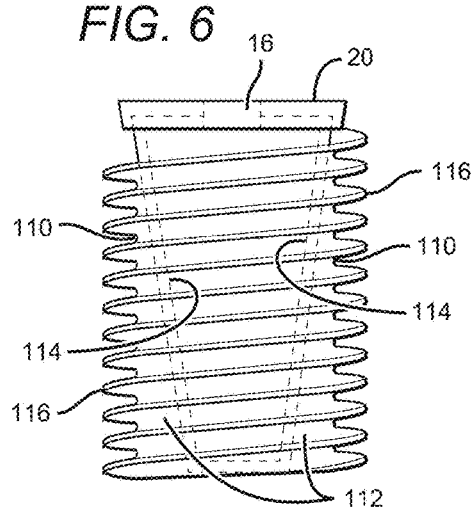
FIG. 6 is a side view of a self-locking cable gripper in a cartridge form.

The cartridge approach requires a means of securely affixing the cartridge to the component. As illustrated in FIG. 6, one possible means is to make the exterior walls 110 of the cable gripper housing 112 cylindrical, while the interior walls 114 remain conical. Threads 116 are then machined into the walls of the cylinder, sized to mate with a corresponding hole which has been formed in the receiving component. The cartridge can then be secured to the component by being screwed into the corresponding hole, and easily removed by being unscrewed. Note that the use of threads is merely one possibility; many other securing means might also be used. For example, such a cartridge could be shrunk fit or press fit onto the component, or a locking taper interlock could be used.

One method of tightening one or more cables around an anatomical structure using only a pair of clasps 100, 102 was discussed above. An alternative tightening method is to use an external tensioning device, such as those described in U.S. Pat. No. 8,469,967 and co-pending patent application Ser. No. 13/925,388, both to Pratt et al. Conventionally, a cable to be tightened with a tensioner is threaded through a gripping mechanism integral to the tensioner, such as a pair of cleats. However, this can subject the tensioner to biological materials, necessitating a thorough and time-consuming cleaning and sterilization process after each use.

Figure 7:
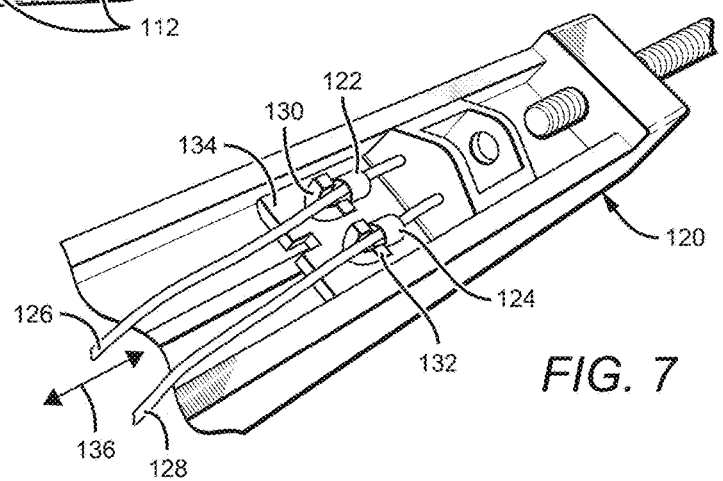
FIG. 7 is a perspective view illustrating the use of two self-locking cable grippers, each in a cartridge form, with a tensioning device.

A cartridge-type cable gripper as described herein could be advantageously used with such a tensioning device, such as device 120 shown in FIG. 7. Here, cartridges 122, 124 would be first threaded onto each cable 126, 128 to be tensioned. The tensioning device would be designed with a feature, such as a yoke or yokes 130, 132, which are mounted on a platform 134 that is translated linearly 136 when the tensioner is adjusted. Each yoke is sized to receive a cable onto which a cable gripper cartridge has been threaded, and to prevent the passage of the cartridge past the yoke when the cable is under tension.

Each cable with pre-installed cartridge is inserted into the tensioning device 120 such that the cartridge 122, 124 abuts a yoke; the position of platform 134 is then adjusted as needed to apply the desired amount of tension to the cable. In this way, direct contact with cables 126, 128 is made via cartridges 122, 124 rather than with an integral gripping mechanism as is the case conventionally, thereby reducing the amount of biological materials to which the tensioning device is subjected.

The present self-locking cable gripper is well-suited for use with flexible cables having a diameter of 1-2 mm, though the design could be easily adapted to cables having different diameters.

As noted above, the present cable gripper is useful for retaining surgical cables under high tension. Many such applications are made substantially easier to execute when the locking mechanism is made automatic as described herein, rather than requiring the use of a manually-inserted clip or crimping tool as is known in the prior art. The present device provides a functional improvement over such prior art methods, due to the ability to avoid the necessity of securing surgical exposure in order to secure the tensioned cable.

Note that, in addition to cerclage, the present cable gripper could be used with surgical cable to provide point-to-point fixation. Here, more than one point, in a series, could be tightened and locked.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

I claim:

1. A self-locking cable gripper, suitable for retaining flexible cables under load, comprising:

a housing having a void which runs between openings at the top and bottom of said housing, said void tapering from a wider portion adjacent said top opening to a narrower portion adjacent said bottom opening;

a collapsible member positioned within said housing adjacent said housing's bottom opening, said collapsible member having a central passage which runs between a top and bottom opening, said housing's bottom opening sized to retain said collapsible member within said housing; and a pair of half jaws distinct from said collapsible member and positioned within said housing between said collapsible member and said housing's top opening, said half jaws sized such that their inner surfaces are urged towards each other when said half jaws are moved toward said housing's bottom opening due to the tapering of said void, said housing's top opening sized to retain said half jaws within said housing;

said housing's top and bottom openings, said collapsible member's top and bottom openings and said central passage, and the inner surfaces of said half jaws defining a channel capable of receiving a cable passed through said housing from said housing's bottom opening to its top opening;

said collapsible member arranged to maintain said half jaws in said wider portion of said void in an 'open' position while said cable is being passed through said housing from its bottom opening to its top opening, and to collapse and thereby allow said half jaws to move toward said housing's bottom opening and be urged towards each other into a 'closed' position when said cable is pulled in the opposite direction.

2. The cable gripper of claim 1, said gripper arranged such that, when said cable which has been passed through said housing from its bottom opening to its top opening is pulled in the opposite direction, said half jaws are drawn toward said housing's bottom opening such that their inner surfaces are urged towards each other, thereby locking said cable in place while it is under tension.

3. The cable gripper of claim 2, wherein outer surfaces of said half jaws are polished such that they slide easily within the housing so as to minimize the creation of wear debris and corrosion products.

4. The cable gripper of claim 2, wherein an inner surface of the housing is polished such that the half jaws slide easily within the housing so as to minimize the creation of wear debris and corrosion products.

5. The cable gripper of claim 1, wherein said housing and said half jaws are manufactured from the same metallic alloy so as to minimize galvanic corrosion.

6. The cable gripper of claim 1, wherein said half jaws are manufactured from an engineered high strength polymer.

7. The cable gripper of claim 1, wherein said half jaws are manufactured from PEEK.

8. The cable gripper of claim 1, wherein said housing is manufactured from an engineered high strength polymer.

9. The cable gripper of claim 8, wherein said housing is manufactured from PEEK.

10. The cable gripper of claim 1, wherein said housing comprises biocompatible metal.

11. The cable gripper of claim 10, wherein said housing comprises titanium or titanium alloy.

12. The cable gripper of claim 1, wherein said collapsible member is dome-shaped, said collapsible member arranged such that said dome collapses when said half jaws move toward said housing's bottom opening.

13. The cable gripper of claim 1, wherein said collapsible member comprises polyethylene.

14. The cable gripper of claim 13, wherein said collapsible member comprises HDP or UHMWP/E.

15. The cable gripper of claim 1, wherein said half jaws comprise biocompatible metal.

16. The cable gripper of claim 15, wherein said half jaws comprise titanium or titanium alloy.

17. The cable gripper of claim 1, wherein the inner surfaces of said half jaws adjacent to said collapsible member are beveled to ease the passage of a cable through said housing from its bottom opening to its top opening.

18. The cable gripper of claim 1, wherein the bottom surface of said housing's top opening is beveled to ease the passage of a cable through said housing from its bottom opening to its top opening.

19. The cable gripper of claim 1, wherein the top surface of said housing's top opening is beveled so that undue stresses are not created in the cable when under tension and exiting the housing at an angle.

20. The cable gripper of claim 1, said jaws arranged such that the channel through said half jaws when in said 'open' position is tapered so as to ease the passage of said cable through said housing from its bottom opening to its top opening.

21. The cable gripper of claim 20, wherein the taper of said channel through said half jaws when in said 'open' position is 3° or less.

22. The cable gripper of claim 1, wherein said housing is conical.

23. The cable gripper of claim 1, wherein said housing's top and bottom openings are circular and said collapsible member's central passage is cylindrical.

24. The cable gripper of claim 1, wherein said housing includes a removable top cap which contains said housing's top opening.

25. The cable gripper of claim 1, wherein said housing includes a top cap which is permanently attached to said housing and contains said housing's top opening.

26. The cable gripper of claim 1, further comprising a securing means for affixing said cable gripper to an external component, said cable gripper with said securing means forming a cartridge.

27. The cable gripper of claim 26, wherein said external component is a bone plate, a prosthesis or a surgical anchor.

28. The cable gripper of claim 26, wherein said securing means comprises threads machined into the exterior walls of said housing.

29. The cable gripper of claim 28, further comprising the external component to which said cartridge is to be secured, said external component adapted to receive said threads and thereby affix said cartridge to said external component.

30. The cable gripper of claim 26, wherein the exterior walls of said housing are cylindrical.

31. The cable gripper of claim 30, wherein said cylindrical exterior walls are said securing means.

32. The cable gripper of claim 26, further comprising a tensioning device to which said cartridge is to be secured, said tensioning device adapted to receive a cartridge which has been threaded onto a cable and to adjust the position of said cartridge to adjust the tension on said cable.

33. The cable gripper of claim 32, wherein said tensioning device comprises one or more yokes, each of which is sized to receive a cable onto which a cartridge has been threaded and to prevent the passage of said cartridge past said yoke when said cable is under tension, said tensioning device arranged to adjust the position of said yokes to adjust the tension on said cable.

34. A self-locking cable gripper clasp assembly, comprising:
at least two self-locking cable grippers, each comprising:
a housing having a void which runs between openings at the top and bottom of said housing, said void tapering from a wider portion adjacent said top opening to a narrower portion adjacent said bottom opening;
a collapsible member positioned within said housing adjacent said housing's bottom opening, said collapsible member having a central passage which runs between a top and bottom opening, said housing's bottom opening sized to retain said dome-shaped member within said housing; and
a pair of half jaws distinct from said collapsible member and positioned within said housing between said collapsible member and said housing's top opening, said half jaws sized such that their inner surfaces are urged towards each other when moved toward said housing's bottom opening due to the tapering of said void, said housing's top opening sized to retain said half jaws within said housing;
said housing's top and bottom openings, said collapsible member's top and bottom openings and said central passage, and the inner surfaces of said half jaws defining a channel capable of receiving a cable passed through said housing from its bottom opening to its top opening;
said collapsible member arranged to maintain said half jaws in said wider portion of said void in an 'open' position while said cable is being passed through said housing from its bottom opening to its top opening, and to collapse and thereby allow said half jaws to move toward said housing's bottom opening and be urged towards each other into a 'closed' position when said cable is pulled in the opposite direction;

said at least two self-locking cable grippers coupled together to form the self-locking cable gripper clasp assembly, said at least two self-locking cable grippers adjacent each other and oriented such that their respective channels are parallel to each other.

35. The clasp assembly of claim 34, said assembly comprising first and second self-locking cable grippers arranged side-by-side, with the orientation of the top and bottom openings of said first gripper's housing being the same as the orientation of the top and bottom openings of said second gripper's housing.

36. The clasp assembly of claim 34, said assembly comprising first and second self-locking cable grippers arranged side-by-side, with the orientation of the top and bottom openings of said first gripper's housing being opposite the orientation of the top and bottom openings of said second gripper's housing.

\* \* \* \* \*